United States Patent
Melker et al.

(10) Patent No.: US 6,915,804 B2
(45) Date of Patent: Jul. 12, 2005

(54) TRACHEOTOMY SURGICAL DEVICE

(75) Inventors: Jeremy S. Melker, Gainesville, FL (US); Richard J. Melker, Gainesville, FL (US)

(73) Assignee: University of Florida, Gainesville, FL (US)

( * ) Notice: Subject to any disclaimer, the term of this patent is extended or adjusted under 35 U.S.C. 154(b) by 68 days.

(21) Appl. No.: 10/308,902

(22) Filed: Dec. 3, 2002

(65) Prior Publication Data

US 2004/0103900 A1 Jun. 3, 2004

(51) Int. Cl.$^7$ .............................................. A61M 16/00
(52) U.S. Cl. ........................ 128/207.29; 128/207.14; 128/207.15; 128/200.26; 600/101; 600/185; 606/45; 606/108; 606/167; 606/185; 604/104.01
(58) Field of Search ................. 128/207.29, 207.14, 128/207.15, 200.26; 600/101, 185; 606/45, 108, 167, 184; 604/164.01

(56) References Cited

U.S. PATENT DOCUMENTS

| | | | | | |
|---|---|---|---|---|---|
| 241,036 | A | * | 5/1881 | Lyman | 128/207.29 |
| 300,285 | A | * | 6/1884 | Russell | 128/207.29 |
| 1,845,727 | A | * | 2/1932 | Slaughter | 27/24.1 |
| 1,867,624 | A | * | 7/1932 | Hoffman | 600/567 |
| 2,052,870 | A | * | 9/1936 | Coco | 606/120 |
| 2,834,349 | A | * | 5/1958 | Springer | 606/174 |
| 2,840,082 | A | * | 6/1958 | Salvatore | 606/140 |
| 2,994,321 | A | * | 8/1961 | Tischler | 600/564 |
| 3,104,666 | A | * | 9/1963 | Hale et al. | 128/207.29 |
| 3,688,773 | A | * | 9/1972 | Weiss | 128/207.29 |
| 3,759,263 | A | * | 9/1973 | Taylor | 128/207.29 |
| 3,835,860 | A | | 9/1974 | Garretson | |
| 3,837,345 | A | * | 9/1974 | Matar | 606/159 |
| 3,888,258 | A | * | 6/1975 | Akiyama | 606/109 |
| 3,916,903 | A | * | 11/1975 | Pozzi | 128/207.29 |
| 4,018,228 | A | * | 4/1977 | Goosen | 606/184 |
| 4,182,337 | A | * | 1/1980 | Nickson | 128/207.29 |
| 4,716,901 | A | * | 1/1988 | Jackson et al. | 606/185 |
| 4,765,334 | A | * | 8/1988 | Weiss | 606/108 |
| 4,877,021 | A | * | 10/1989 | Higer et al. | 128/200.26 |
| 4,889,112 | A | | 12/1989 | Schachner et al. | |
| 5,192,294 | A | * | 3/1993 | Blake, III | 606/184 |
| 5,242,427 | A | * | 9/1993 | Bilweis | 604/264 |
| 5,289,963 | A | | 3/1994 | McGarry et al. | |
| 5,334,198 | A | * | 8/1994 | Hart et al. | 606/52 |
| 5,392,978 | A | | 2/1995 | Velez et al. | |
| 5,403,338 | A | * | 4/1995 | Milo | 606/184 |
| 5,558,081 | A | | 9/1996 | Lipkin | |
| 5,618,304 | A | * | 4/1997 | Hart et al. | 606/52 |
| 5,681,323 | A | * | 10/1997 | Arick | 606/108 |
| 5,893,876 | A | | 4/1999 | Turkel et al. | |
| 5,910,153 | A | * | 6/1999 | Mayenberger | 606/184 |
| 5,972,014 | A | * | 10/1999 | Nevins | 606/185 |
| 5,988,168 | A | * | 11/1999 | Bair | 128/207.29 |
| 6,080,173 | A | | 6/2000 | Williamson, IV et al. | |
| 6,802,846 | B2 | * | 10/2004 | Hauschild et al. | 606/110 |

FOREIGN PATENT DOCUMENTS

GB     2 365 352     2/2002

* cited by examiner

*Primary Examiner*—Henry Bennett
*Assistant Examiner*—Nihir Patel
(74) *Attorney, Agent, or Firm*—Timothy H. Van Dyke; Beusse Brownlee Wolter Mora & Maire

(57) ABSTRACT

Disclosed herein is a novel surgical instrument, and method of using same, designed for performing tracheotomy. According to specific embodiments, the subject surgical instrument comprises a novel foot plate that is anatomically curved to follow the contours of the inner wall of the trachea.

11 Claims, 4 Drawing Sheets

FIG.3
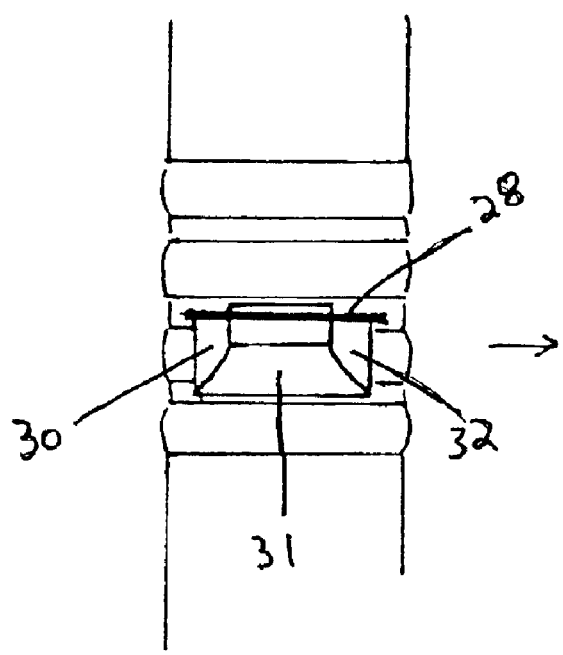 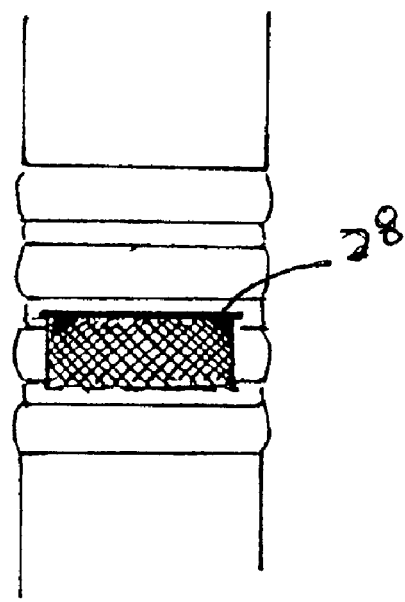
FIG.4

TRACHEOTOMY SURGICAL DEVICE

FIELD OF THE INVENTION

The subject invention relates to the field of surgical devices in the area of tracheotomy procedures.

BACKGROUND

A tracheotomy is a surgical procedure that creates a temporary or permanent opening in the trachea. The aperture created and the tube positioned in the aperture are together called a tracheostomy. The tube that is placed through this hole is commonly called a tracheotomy tube. The history of tracheotomy stretches over several centuries as one of the oldest of surgical procedures. A tracheotomy was even pictured on Egyptian tablets in 3600 B.C. However, it was Asclepiades of Persia in 100 BC who is credited as the first person to perform this procedure. The procedure was originally used for the emergency management of upper airway obstruction although with limited success. The term tracheotomy was not used until Lorenz Heister coined the term in 1718. M. Sicard, Ground Rounds Archives, "Complications of Tracheotomy", Dec. 1, 1994, www.bcm.tmc.edu/oto/grand/12194.html.

A tracheotomy is performed for a variety of reasons including, but not limited to, the following:

1. To bypass an obstruction in the airway;
2. To help with long term ventilation in patients who cannot do this on their own (patients with respiratory muscle problems or lung problems); or
3. To provide a temporary airway while reconstructive surgery is performed that may cause breathing problems.

Tracheotomy is traditionally performed in a hospital setting by a physician who has extensive experience in this procedure, and is typically performed by an ear, nose and throat specialist (Otolaryngologist) or General Surgeon. Traditionally, a patient undergoing tracheotomy is placed on their back and a rolled towel, or similar support, is placed under the shoulders in order to extend the neck and bring the trachea in its most accessible position. Dissection is first carried through the skin and subcutaneous fat until muscles overlying the airway are identified. These are separated in the midline, exposing the central portion of the thyroid gland which typically must be divided in order to gain access to the anterior tracheal wall. Depending on the preference of the surgeon a horizontal or vertical incision is carefully made in a specific location in the trachea with a scalpel. Again, according to the preference of the surgeon and the patient's body habitus, stay sutures (stitches) may be placed adjacent to the incision. These are tied and secured to the patient's chest and are intended to add a margin of safety in the event of tracheostomy tube displacement. In this situation, the sutures allow the anterior tracheal wall and tracheotomy site to be pulled up to the skin level, reducing the risk of placement of a the tracheostomy tube in a "false passage" within the subcutaneous tissues of the neck. Stay sutures are typically removed 3–5 days after the procedure once a mature scar tissue tract has formed from the skin to the tracheotomy site (tracheostoma) and tube replacement therefore becomes less risky. Under direct visualization through the tracheotomy site, the transoral endotracheal tube is backed out of the airway, and a tracheostomy tube placed by the surgeon. Finally, the tracheostomy tube is sutured to the skin and secured with a tie around the patient's neck. Sometimes, a chest x-ray is taken to check for proper placement.

Early Complications that may arise during the tracheotomy procedure or soon thereafter include:

Bleeding (typically from injury to subcutaneous veins encountered during the procedure or secondary to inadequate hemostasis upon division of the extremely vascular thyroid gland)

Air trapped underneath the skin (subcutaneous emphysema) or within the fascial layers of the neck and chest (pneumomediastinum) around the tracheotomy if difficulty is encountered while placing the tracheostomy tube resulting in air leak.

Air leak within the pleural cavity and subsequent lung collapse (pneumothorax) may result from direct injury to the apices of the lungs, which may extend above the clavicles, particularly in thin patients.

Damage to the tube going to the stomach (esophagus), which shares a common wall with the posterior trachea, may result from excessive force during tracheostomy tube placement.

Injury to the nerves that move the vocal cords (recurrent laryngeal nerves) which course along the lateral aspect of the trachea and may be injured if a horizontal tracheal incision is carried too far laterally.

The conventional tracheotomy procedure involves entering the trachea with a scalpel and then cutting of the trachea tissue and cartilage ring(s) with either a scalpel or surgical scissors. With age, the cartilage rings of the trachea tend to calcify, which can make precise cutting extremely difficult. The conventional tracheotomy procedure can lead to scarring, which may be brought about by imprecise cutting of the trachea. The tracheotomy is an old procedure that has gone unchanged for decades. There is a need for new techniques and surgical instruments that can make the tracheotomy procedure quicker, more precise, and, most importantly, safer for patients.

SUMMARY OF THE INVENTION

The subject invention relates to a novel surgical device for performing a tracheotomy procedure. One aspect of the subject invention pertains to an instrument comprising a two-piece punch positioned at one end of the instrument. The two-piece punch comprises a first element which contacts the tissue from the outside, and a second element which is inserted into the trachea via an incision between the cartilage rings of the trachea. The first element is configured so that it is opposed to the second element and aligned such that when the first and second elements are brought together, a section of tissue of the trachea is cut or "punched". Either the first element or the second element comprises a cutting edge. Preferably, the first element comprises a cutting edge thereby effecting a cut from the outside in. The second element preferably comprises a foot plate. Even more preferred, the foot plate is curved such that it corresponds to the curvature of the inside of the trachea.

In a specific embodiment, the surgical instrument comprises an elongated body comprising a forward and a rearward end, and a handle extending transversely from said elongated body at a position proximal to said rearward end. According to this embodiment, the elongated body comprises a first elongated shaft portion and a second elongated shaft portion, wherein said first elongated shaft portion is configured such that it is longitudinally slidable with respect to said second elongated shaft portion. The first elongated shaft portion preferably comprises a cutting portion integral with or attached to said first elongated shaft portion at its forward end. The second elongated shaft comprises a foot plate that is integral with or attached to said elongated shaft at is forward end. The surgical instrument comprises a handle mounted to said elongated body. The handle comprises at least one lever portion that is engaged to or integral with said first shaft portion or second shaft portion, or both wherein upon actuation of said lever, said cutting portion of said first elongated shaft portion foot plate are drawn toward each other thereby punching a window in the trachea of said patient.

Preferably, but not necessarily, the cutting portion comprises two cutting edges configured such that when the foot plate and said cutting portion are brought together, a rectangular shaped window is created in the trachea of said patient with a flap of tissue connected at the inferior aspect of said window. The flap of tissue, known as a Bjork flap in a described modification of the procedure, is sutured to the inferior aspect of the skin incision. The intent is to allow safer replacement of a dislodged tube by approximating the anterior tracheal wall to the skin and obliterating a potential "false passage" in the subcutaneous tissues of the neck. Alternatively, the cutting portion comprises three cutting edges configured as a rectangle whereby a complete section of tissue is cut out when the foot plate and cutting portion are brought together. Those skilled in the art will appreciate that other designs for the cutting edge may be implemented, including but not limited to a single cutting edge that is curved, whereby an arcuate section of tissue is cut.

Furthermore, subglottic stenosis or in severe cases, tracheal atresia, is a possibility whenever the framework of the trachea's cartilaginous structure is violated. See for example, Klussmann, et al., *Chest* 2001; 119:961–964. It is believed that the chances of scarring and stenosis are decreased by reducing the extent of injury to the trachea. The subject invention minimizes injury to the trachea by cutting a precise window. Ergo, it is believed that the subject invention will reduce the chances of scarring and stenosis in the trachea.

These and other advantageous aspects of the subject invention are described in further detail below.

DESCRIPTION OF THE DRAWINGS

FIG. 3 is a top cross-sectional view of the forward portion of the embodiment shown in FIG. 2 as positioned in a trachea.

FIG. 4 represents a top view of punched out window in the trachea after the tracheotomy procedure is conducted.

FIG. 5 shows the novel foot plate that is anatomically contoured to follow the curvature of the inside wall of the trachea.

DESCRIPTION OF THE PREFERRED EMBODIMENTS

Except where noted otherwise, the materials utilized in the components of the subject surgical instrument generally include such materials as polycarbonate, or similar plastics for housing sections and related components, and stainless steel for such components which transmit forces. One preferred polycarbonate material is LEXAN brand polycarbonate available from General Electric Company. Other specific preferred materials such as nylon or glass filled nylon (for strength) are also utilized. However, equivalent alternative materials will readily come to the mind of those skilled in the art. As related hereinabove, current injection molding and metalplas insert molding techniques can be used to provide a high quality disposable instrument. Preferably, the cutting edges of the subject surgical instrument are made of metal.

Figure 1:
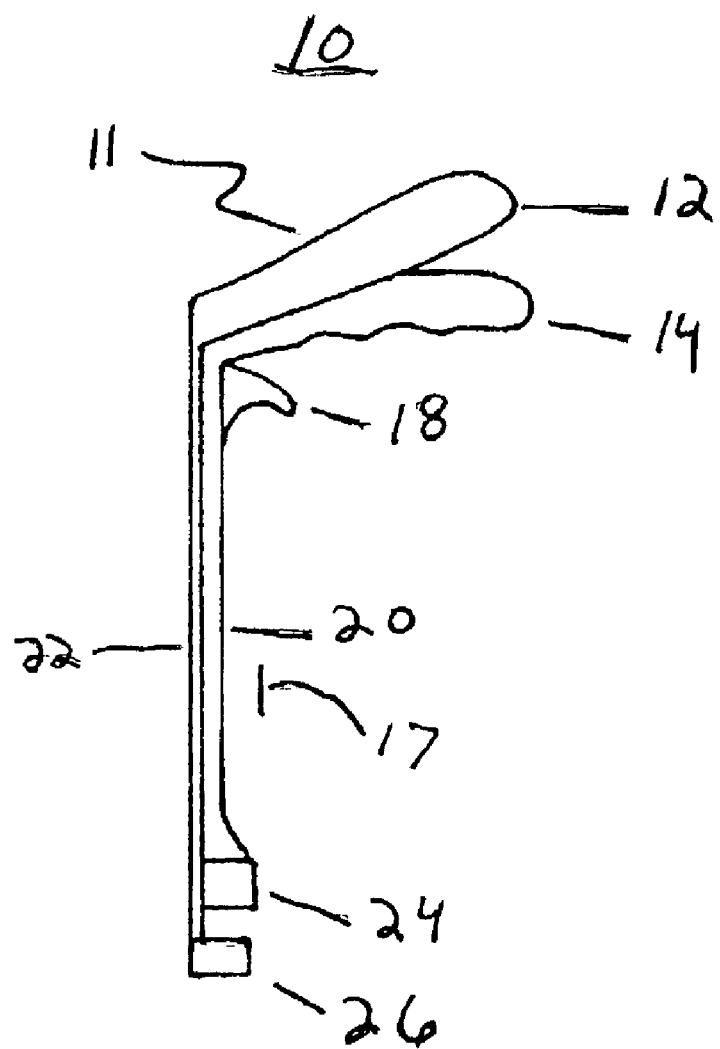
FIG. 1 is a full side view of one embodiment of the subject tracheotomy surgical instrument.

The subject invention is directed toward a surgical instrument for performing a tracheotomy procedure on a patient in need thereof. Turning to FIG. 1, a surgical instrument embodiment 10 is shown. Embodiment 10 comprises a body portion 17. The body portion comprises a first shaft 20 and second shaft 22. Furthermore, the first shaft 20 and second shaft 22 may be contained within a housing (not shown) such as a tubular casing. At the forward end of the first shaft 20, a cutting portion 24 is attached to or integral with the first shaft 20. At the forward end of the second shaft 22, a foot plate 26 is attached to or integral with the second shaft 22. At the rearward end of the body portion 17, embodiment 10 comprises a handle 11. As shown in FIG. 1, the handle comprises a first lever 12 and second lever 14 and, alternatively, a trigger 18. In a specific embodiment, second lever 14 remains static and first lever 12 pivots toward and away from lever portion 14. Squeezing the lever 12 toward lever 14 acts to draw the cutting portion 24 toward the foot plate 26. Alternatively, the first lever 12 is static while the 14 lever is configured to pivot toward the first lever 12.

Those skilled in the art will appreciate that the design and mechanics of the handle portion can take several different configurations. Examples of handle configurations include those used in endoscopic staplers, as shown in U.S. Pat. Nos. 5,392,978 and 5,289,963. For example, those skilled in the art will appreciate that either through pulling of a trigger, or squeezing of the lever portions, a spring loaded firing mechanism could be designed such that the trachea is punched upon actuating the firing mechanism. The actual mechanism used is not important, so long as it carries out the primary objective of sliding the first shaft or the second shaft, or both simultaneously, such that the cutting portion 24 and the foot plate 26 are brought together.

Figure 2:
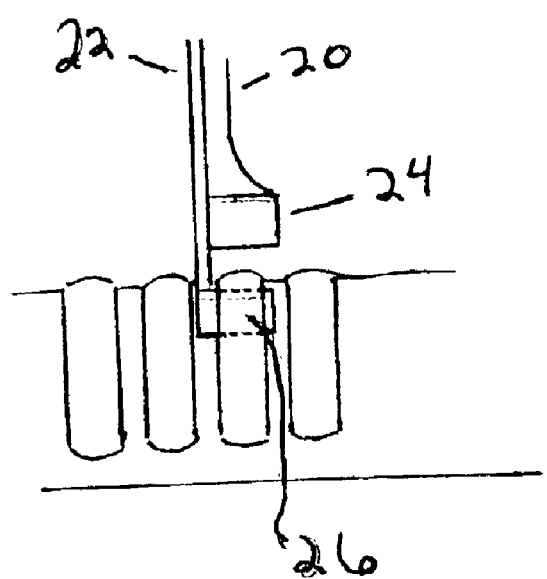
FIG. 2 is a side view of the forward end of the embodiment shown in FIG. 1 as positioned in a trachea.

During operation, a horizontal incision is made in the trachea of a patient and the foot plate 26 is inserted into the trachea through the incision (see FIG. 2). The incision is typically made just large enough to accommodate the foot plate 26. The foot plate is then abutted against the interior wall of the trachea and the cutting portion 24 is positioned on the exterior of the trachea. When the lever 12 of handle 11 is actuated, the cutting portion 24 is drawn to the foot plate 26. The tissue between the cutting portion 24 and the foot plate 26 is cut in a "punch-like" fashion. The subject instrument creates a precise window incision or window/flap incision by just a single maneuver.

Figure 5:
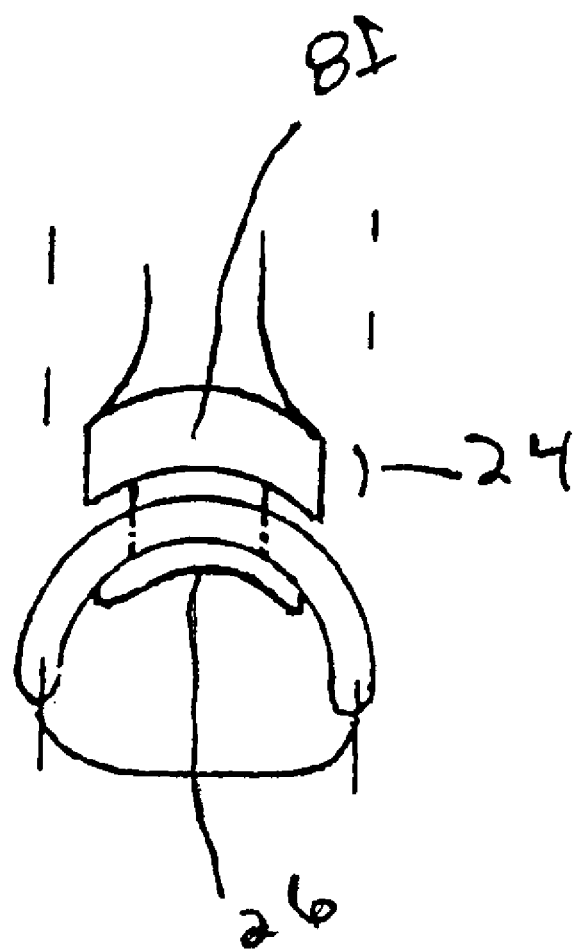
FIG. 5 represents a bottom view of an embodiment of the subject surgical instrument as positioned in the trachea.

The foot plate 26 may be flat, but is preferably curved as shown in FIG. 5. The curved foot plate 26 provides increased stability when the subject surgical instrument is properly position on the trachea, which results in increased accuracy for the punch-out as the tracheotomy procedure is conducted. To optimize the stability of the subject surgical instrument, the foot-plate should be curved such that it follows the contours of the inner wall of the trachea, i.e., it is "anatomically configured". Preferably, but not necessarily, the cutting portion 24 comprises at least two cutting edges. In a particularly preferred embodiment shown in FIG. 3, the cutting portion comprises three cutting edges: vertically oriented edges 30 and 32, and horizontally-oriented edge 31. The cutting edges 30, 31, and 32 are configured such that when the foot plate and said cutting portion are brought together, and aligned with the incision 28, a rectangular shaped window 34 is created in the trachea of the patient, as shown in FIG. 4. Alternatively, the cutting portion 24 is provided with only two edges, e.g. cutting edge 31 is missing, which creates a flap of tissue connected at the inferior side of the punched-out window. Furthermore, as shown in FIG. 5, horizontal cutting edge 81 may also be anatomically curved to follow the contours of the outer surface of the trachea. Alternatively, skilled artisans will appreciate that other designs for the cutting edge may be implemented, including but not limited to a single cutting edge that is curved, whereby an arcuate section of tissue is cut.

Furthermore, the cutting edges and configuration can be provided in various sizes. For example, cutting portion and cutting edges may be of a size specifically intended for use in infants or children, or of a size specifically intended for adults. Also, the cutting portion is sized and configured for cutting just one cartilage ring of the tissue. However, in unique circumstances, it may be desirous to cut two or more cartilage rings in forming the tracheotomy window. The subject instrument, particularly the cutting the portion, can be designed and sized to create larger punch outs as needed.

In an alternative embodiment, the cutting portion comprises a single cutting edge that is arcuate or semi-arcuate. The arcuate cutting edge and foot plate can be configured such that when the punch is actuated a semi-circular or circular shaped window is cut.

Furthermore, another embodiment comprises a surgical instrument that comprises a cutting portion having four cutting edges. One advantage of using this alternative embodiment allows for the surgeon to create a small incision in the trachea, ideally just large enough to insert the foot plate into. Upon placement of the surgical instrument and actuation of the lever, the four cutting edges create a complete window in the trachea. If the surgeon makes a small or uneven incision, the four cutting edges alleviate problems caused by skin or other tissue that may be left intact. It is believed that the smaller incision will also minimize scarring. In view of the teachings herein, it will be understood that the incision can be dilated if it is unable to accommodate the foot plate. Other configurations are contemplated in view of the teachings herein. For example the surgical instrument may be designed such that a small incision is made and the foot plate is inserted from a lateral direction, as opposed to above or below the intended excision area. This allows for a smaller incision and a clean "cut" on three sides (when leaving a flap is intended) or four sides (when a complete window punch is intended).

The teachings of the references cited throughout the specification are incorporated herein by this reference to the extent they are not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A surgical instrument for performing a tracheotomy procedure on a patient in need thereof comprising:
   an elongated body comprising a forward and a rearward end, and a handle extending transversely from said elongated body at a position proximal to said rearward end; said elongated body comprising a first shaft and a second shaft, wherein said first shaft and said second shaft portion are secured such that the first shaft is longitudinally moveable;
   a cutting portion integral with or attached to said first shaft at its forward end, said cutting portion comprising at least two cutting edges;
   a foot plate integral with or attached to said second shaft at its forward end; and
   a handle mounted to said body portion, said handle comprising a lever communicatingly engaged to or integral with said first shaft, wherein upon actuation of said lever, said cutting portion of said first shaft is drawn toward said foot plate, thereby punching a window in the trachea of said patient.

2. The surgical instrument of claim 1, wherein said cutting portion comprises two cutting edges configured such that a rectangular shaped window is created in the trachea of said patient with a flap of tissue connected at one side of said window.

3. The surgical instrument of claim 2, wherein said cutting portion comprises three cutting edges: a horizontally oriented cutting edge comprising a left end and a right end; a left vertically oriented cutting edge attached to or integral with said left end; and a right vertically oriented cutting edge attached to or integral with said right end.

4. The surgical instrument of claim 3, wherein said horizontally oriented cutting edge is anatomically curved such that said horizontally oriented cutting edge follows the contours of the outer surface of the trachea.

5. The surgical instrument of claim 1, wherein said foot plate is anatomically curved to follow the contours of the inner wall of the trachea.

6. The surgical instrument of claim 1, wherein said cutting portion comprises one curved cutting edge configured such that a partially arcuate shaped window is created in the trachea of said patient.

7. A method of performing a tracheotomy in a patient in need thereof comprising:
   a) forming an incision between an upper and lower cartilage ring of said patient's trachea; and
   b) positioning a surgical instrument onto said trachea; wherein said surgical instrument comprises:
      an elongated body comprising a forward and a rearward end, and a handle extending transversely from said elongated body at a position proximal to said rearward end; said elongated body comprising a first shaft and a second shaft, wherein said first shaft and said second shaft portion are disposed such that the first shaft is longitudinally moveable;
      a cutting portion integral with or attached to said first shaft at its forward end, said cutting portion comprising at least two cutting edges;
      a foot plate integral with or attached to said elongated shaft at its forward end; and
      a handle mounted to said body portion, said handle comprising a lever communicatingly engaged to or integral with said first shaft, wherein upon actuation of said lever, said cutting portion of said first shaft is drawn toward said foot plate;
   wherein said positioning comprises insertion of said foot plate into said trachea through said incision.

8. The method of claim 7 further comprising the step of actuating said lever, thereby punching a window in said trachea.

9. A surgical instrument for performing a tracheotomy procedure on a patient in need thereof comprising:
   an elongated body comprising a forward and a rearward end, and a handle extending transversely from said elongated body at a position proximal to said rearward end; said elongated body comprising a first shaft and a second shaft, wherein said first shaft and said second shaft portion are disposed such that the second shaft is longitudinally moveable;

a cutting portion integral with or attached to said first shaft at its forward end, said cutting portion comprising at least two cutting edges;

a foot plate integral with or attached to said elongated shaft at its forward end; and a handle mounted to said body portion, said handle comprising a lever communicatingly engaged to or integral with said second shaft, wherein upon actuation of said lever, said foot plate on said second shaft is drawn toward said cutting portion, thereby punching a window in the trachea of said patient.

10. The surgical instrument of claim 9, wherein elongated body portion comprises a casing, wherein said first and second shaft are housed in said casing.

11. The surgical instrument of claim 10, wherein said casing is tubular.

* * * * *